(12) United States Patent
Kobayashi et al.

(10) Patent No.: US 11,771,431 B2
(45) Date of Patent: Oct. 3, 2023

(54) ANASTOMOSIS ASSIST TOOL AND VASCULAR ANASTOMOSIS METHOD

(71) Applicant: SCREEN HOLDINGS CO., LTD., Kyoto (JP)

(72) Inventors: Eiji Kobayashi, Kyoto (JP); Hiroo Kasamatsu, Kyoto (JP); Shinji Torai, Kyoto (JP); Syuhei Yoshimoto, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 31 days.

(21) Appl. No.: 17/702,284

(22) Filed: Mar. 23, 2022

(65) Prior Publication Data

US 2022/0218353 A1    Jul. 14, 2022

Related U.S. Application Data

(62) Division of application No. 16/608,547, filed as application No. PCT/JP2018/015597 on Apr. 13, 2018, now abandoned.

(30) Foreign Application Priority Data

Apr. 28, 2017  (JP) ................................. 2017-089957
Mar. 19, 2018  (JP) ................................. 2018-050364

(51) Int. Cl.
*A61B 17/11*    (2006.01)
*A61B 17/00*    (2006.01)

(52) U.S. Cl.
CPC ..... *A61B 17/11* (2013.01); *A61B 2017/00292* (2013.01); *A61B 2017/1107* (2013.01)

(58) Field of Classification Search
CPC ............ A61B 17/11; A61B 2017/1107; A61B 2017/1132; A61B 2017/1135; A61B 2017/1139; A61B 2017/1103
See application file for complete search history.

(56) References Cited

U.S. PATENT DOCUMENTS

| 4,398,910 A | 8/1983 | Blake et al. |
| 4,459,978 A | 7/1984 | Kotsanis |

(Continued)

FOREIGN PATENT DOCUMENTS

| EP | 0 750 919 A2 | 1/1997 |
| JP | 60-036039 A | 2/1985 |

(Continued)

OTHER PUBLICATIONS

U.S. PTO Non-Final Office Action issued in related parent U.S. Appl. No. 16/608,547, dated Sep. 14, 2021.

(Continued)

*Primary Examiner* — Diane D Yabut
*Assistant Examiner* — Christina C Lauer
(74) *Attorney, Agent, or Firm* — McDermott Will & Emery LLP

(57) ABSTRACT

An anastomosis assist tool comprises a body unit extending in a predetermined advancing direction, and an insertion unit arranged at the tip of the body unit. The body unit includes an anastomosis assist part having an approximately constant cross-sectional shape in a plane perpendicular to the advancing direction. The anastomosis assist part includes a projection projecting outwardly as viewed in the cross section and extending in the advancing direction. The insertion unit includes a tapered part of a diameter decreasing gradually toward a tip. When the insertion unit and a part of the body unit are inserted into a vessel, the projection of the anastomosis assist part of the body unit abuts on the inner wall of the vessel. This makes it unlikely that the inner wall of the vessel will stick to the body unit at a site other than a point abutting on the projection.

7 Claims, 12 Drawing Sheets

(56) References Cited

U.S. PATENT DOCUMENTS

| | | | |
|---|---|---|---|
| 4,624,255 A * | 11/1986 | Schenck | A61B 17/11 606/155 |
| 5,192,289 A * | 3/1993 | Jessen | A61B 17/11 606/155 |
| 5,755,682 A * | 5/1998 | Knudson | A61B 17/12045 604/8 |
| 5,944,019 A | 8/1999 | Knudson et al. | |
| 6,319,193 B1 | 11/2001 | Arai et al. | |
| 6,869,437 B1 | 3/2005 | Hausen et al. | |
| 9,138,230 B1 | 9/2015 | Buelna | |
| 2015/0157324 A1 * | 6/2015 | Cully | A61B 17/11 606/153 |

FOREIGN PATENT DOCUMENTS

| | | | | |
|---|---|---|---|---|
| JP | 09-70438 A | | 3/1997 | |
| JP | 10-146350 A | | 6/1998 | |
| JP | 11-000335 A | | 1/1999 | |
| JP | 2000-333965 | * | 5/1999 | ............ A61B 17/11 |
| JP | 2000-333965 A | | 12/2000 | |
| JP | 2005-160821 A | | 6/2005 | |
| JP | 2016-538955 A | | 12/2016 | |
| WO | 99/63895 A1 | | 12/1999 | |
| WO | 2015/090338 A1 | | 6/2015 | |

OTHER PUBLICATIONS

U.S. PTO Final Office Action issued in related parent U.S. Appl. No. 16/608,547, dated Dec. 29, 2021.

Entire U.S. PTO in related parent U.S. Appl. No. 16/608,547, filed Oct. 25, 2019.

International Search Report issued in corresponding International Patent Application No. PCT/JP2018/015597, dated Jun. 26, 2018, with English translation.

Japanese Notification of Reason for Refusal issued in corresponding Japanese Patent Application No. 2017-089957, dated Dec. 12, 2017.

Eiji Kobayashi, "In-Site Perfusion Technique for Rinse Solution in Lover Transplantation", Transplantation Direct 2017, pp. 1-2, Mar. 1, 2017.

Extended European Search Report issued in corresponding European Patent Application No. 18790283.8-1122, dated Mar. 13, 2020.

Japanese Notice of Reasons for Refusal issued in corresponding Japanese Patent Application No. 2018-204289, dated Oct. 26, 2021, with English translation.

* cited by examiner

ANASTOMOSIS ASSIST TOOL AND VASCULAR ANASTOMOSIS METHOD

CROSS REFERENCE TO RELATED APPLICATIONS

This application is a Divisional of U.S. patent application Ser. No. 16/608,547 filed Oct. 25, 2019, which is the U.S. National Phase under 35 U.S.C. § 371 of International Application No. PCT/JP2018/015597 filed on Apr. 13, 2018, which claims the benefit of Japanese Application No. 2017-089957, filed on Apr. 28, 2017 and Japanese Application No. 2018-050364 filed on Mar. 19, 2018, the entire contents of each are hereby incorporated by reference.

TECHNICAL FIELD

The present invention relates to an anastomosis assist tool and a vascular anastomosis method using the anastomosis assist tool.

BACKGROUND ART

In various types of surgery such as organ transplant, vessels may be connected to each other through anastomosis. There is a method called triangular anastomosis known as a method of anastomosing vessels. According to the triangular anastomosis, each of the two vessels to be anastomosed is pulled at three points to form a cross section of each of the vessels to be sutured into a triangular shape, and corresponding sides are sutured together.

In some cases of surgery such as organ transplant surgery, while a catheter is inserted into either of two vessels and a liquid is fed, the two vessels are sutured together. A conventional catheter for liquid feed is disclosed in patent literature 1, for example.

CITATION LIST

Patent Literature

Patent Literature 1: Japanese Patent Application Laid-Open No. 7-70438 (1995)

SUMMARY OF INVENTION

Technical Problem

In many conventional catheters including a balloon catheter disclosed in patent literature 1, a catheter body to be inserted into a vessel has a cylindrical outer peripheral surface. Hence, if the inner wall of the vessel sticks to this outer peripheral surface, it becomes difficult to perform triangular anastomosis involving pulling at three points.

For implementation of triangular anastomosis, independently of the presence or absence of insertion of a catheter, suture threads put over respective three points of two vessels are required to be pulled under tension. To achieve this, a hand or a tool for holding each of the suture threads is located around an operative field, causing the risk of reduced workability of surgery. This extends a duration of the surgery, making it difficult to reduce damage on a vessel and an organ connected to the vessel.

The present invention has been made in consideration of the foregoing circumstances, and is intended to provide a technique for increasing workability of vascular anastomosis surgery.

Solution to Problem

To solve the foregoing problem, a first aspect of the present invention is intended for an anastomosis assist tool comprising: a body unit extending in a predetermined advancing direction and having a part to be inserted into a vessel; and an insertion unit arranged at the tip of the body unit. The insertion unit includes a tapered part of a diameter decreasing gradually toward a tip. The body unit includes an anastomosis assist part having an approximately constant cross-sectional shape in a plane perpendicular to the advancing direction. The anastomosis assist part includes a projection projecting outwardly as viewed in the cross section and extending in the advancing direction.

A second aspect of the present invention is intended for the anastomosis assist tool according to the first aspect wherein the projection of the anastomosis assist part includes two, three, or four projections.

A third aspect of the present invention is intended for the anastomosis assist tool according to the second aspect wherein the projections of the anastomosis assist part include three projections.

A fourth aspect of the present invention is intended for the anastomosis assist tool according to the third aspect wherein the cross section of the anastomosis assist part is a regular triangle.

A fifth aspect of the present invention is intended for the anastomosis assist tool according to any one of the first to fourth aspects wherein the projection is arranged uniformly in a peripheral direction.

A sixth aspect of the present invention is intended for the anastomosis assist tool according to any one of the first to fifth aspects wherein the insertion unit further includes a cylindrical part arranged closer to a rear end than the tapered part and having a cylindrical outer peripheral surface.

A seventh aspect of the present invention is intended for the anastomosis assist tool according to any one of the first to sixth aspects wherein the body unit includes a first linear part extending in a linear shape, a bent part bent in a curved shape, and a second linear part extending in a linear shape arranged in this order as viewed from the tip toward a rear end.

An eighth aspect of the present invention is intended for the anastomosis assist tool according to the seventh aspect wherein the angle of the advancing direction of the body unit changes in a range from 90 to 180° at the bent part.

A ninth aspect of the present invention is intended for the anastomosis assist tool according to any one of the first to eighth aspects wherein the anastomosis assist part has flexibility.

A tenth aspect of the present invention is intended for the anastomosis assist tool according to any one of the first to ninth aspects wherein the anastomosis assist part has a surface subjected to surface treatment.

An eleventh aspect of the present invention is intended for the anastomosis assist tool according to any one of the first to tenth aspects further comprising: a lumen extending in the advancing direction and connecting a first opening arranged at the tip and a second opening arranged at a rear end.

A twelfth aspect of the present invention is intended for the anastomosis assist tool according to the eleventh aspect wherein the lumen has a circular cross section in a plane perpendicular to the advancing direction.

A thirteenth aspect of the present invention is intended for a vascular anastomosis method using the anastomosis assist tool according to the third aspect or the fourth aspect wherein the three projections include a first corner, a second corner, and a third corner. The method comprises: a) a step of continuously suturing a site of a first vessel from a point facing the second corner to a point facing the third corner and a corresponding site of a second vessel together while the anastomosis assist tool is inserted in the first vessel; and b) a step of continuously suturing a site of the first vessel from a point facing the first corner to the point facing the second corner and a corresponding site of the second vessel together while the anastomosis assist tool is inserted in the first vessel.

A fourteenth aspect of the present invention is intended for the vascular anastomosis method according to the thirteenth aspect further comprising: c) a step of continuously suturing at least a part of a site of the first vessel from the point facing the first corner to the point facing the third corner and at least a part of a corresponding site of the second vessel together with a suture thread in a loosened state while the anastomosis assist tool is inserted in the first vessel, the step c) being performed after the step a) and the step b); d) a step of pulling the anastomosis assist tool out of the first vessel after the step c); and e) a step of tightening the suture thread after the step d).

A fifteenth aspect of the present invention is intended for the vascular anastomosis method according to the thirteenth aspect or the fourteenth aspect wherein, in the step a), the first corner is placed on a near side in an operative field, and the site of the first vessel from the point facing the second corner to the point facing the third corner is defined as a rear wall.

Advantageous Effects of Invention

According to the first to twelfth aspects of the present invention, the projection abuts on the inner wall of a vessel. This makes it unlikely that the inner wall of the vessel will stick to the body unit at a site other than a point abutting on the projection. This facilitates anastomosis at this site. Namely, workability of vascular anastomosis surgery can be increased.

In particular, according to the second aspect of the present invention, the inner wall of the vessel does not stick to the body unit at a site of the inner wall between points abutting on the projections. This facilitates anastomosis at this site. Namely, workability of vascular anastomosis surgery can be increased.

In particular, the third aspect of the present invention facilitates implementation of triangular anastomosis surgery.

In particular, according to the fourth aspect and the fifth aspect of the present invention, if the anastomosis assist tool is inserted into the vessel in a wrong direction, the uniform arrangement of the projection or the projections facilitates adjustment of the direction of the insertion.

In particular, according to the sixth aspect of the present invention, ligation of the vessel is facilitated at the cylindrical part.

In particular, according to the seventh aspect and the eighth aspect of the present invention, as the advancing direction is changed at the bent part, surgery is unlikely to be hindered by a part not inserted into the vessel. Thus, workability of vascular anastomosis surgery can be increased.

In particular, according to the ninth aspect of the present invention, the flexibility of the anastomosis assist part reduces the occurrence of damage on the vessel. Further, the anastomosis assist tool is easily movable to an intended position during surgery.

In particular, according to the tenth aspect of the present invention, as the anastomosis assist part is subjected to surface treatment, it becomes unlikely that a surgical needle will be hooked to or will stick into the body unit. This increases workability of surgery.

In particular, the eleventh aspect of the present invention allows supply or suction of a liquid such as a perfusate into or from the vessel through the anastomosis assist tool.

In particular, the twelfth aspect of the present invention suppresses increase in a resistance at a liquid flow path in the lumen.

According to the thirteenth to fifteenth aspects of the present invention, workability is increased during triangular anastomosis surgery.

DESCRIPTION OF EMBODIMENTS

Figure 1:
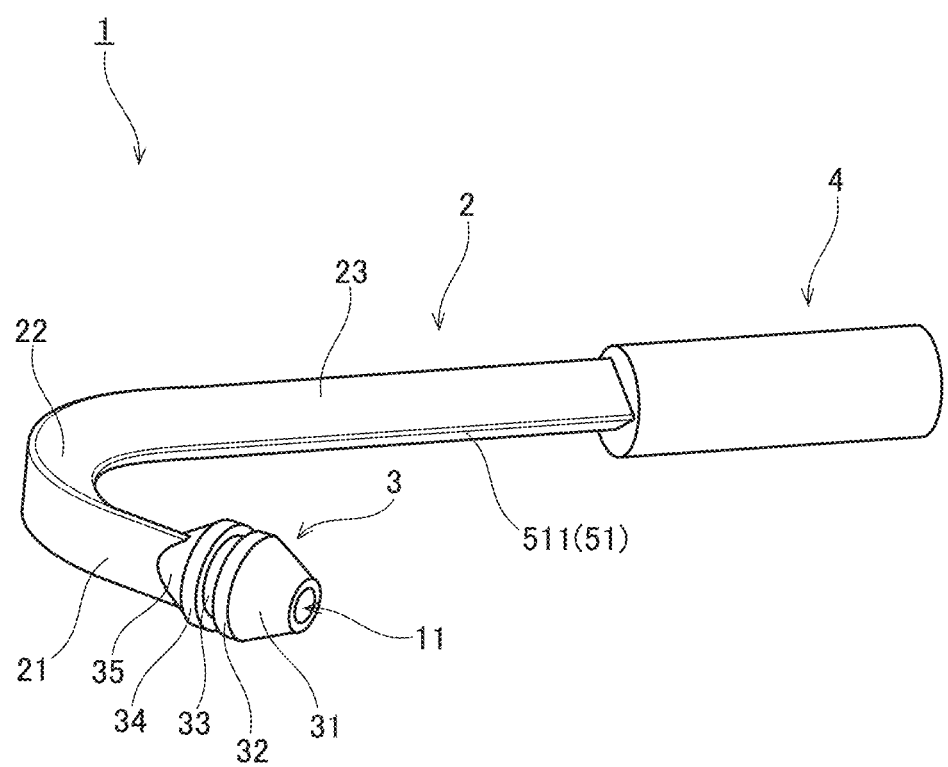
FIG. 1 is a perspective view of a catheter connecting member according to a first embodiment.

An embodiment of the present invention will be described below by referring to the drawings. "Donors" and "recipients" mentioned in the present invention may either be humans or non-human animals. More specifically, in the present invention, "organs" including livers may be human organs or organs of non-human animals. Further, in the present invention, "vessels" may be human vessels or vessels of non-human animals. Non-human animals may be rodents including mice and rats, ungulate animals including pigs, goats, and sheep, non-human primates including chimpanzees, other types of non-human mammals, and animals other than mammals.

1. First Embodiment

<1-1. Configuration of Catheter Connecting Member>

Figure 2:
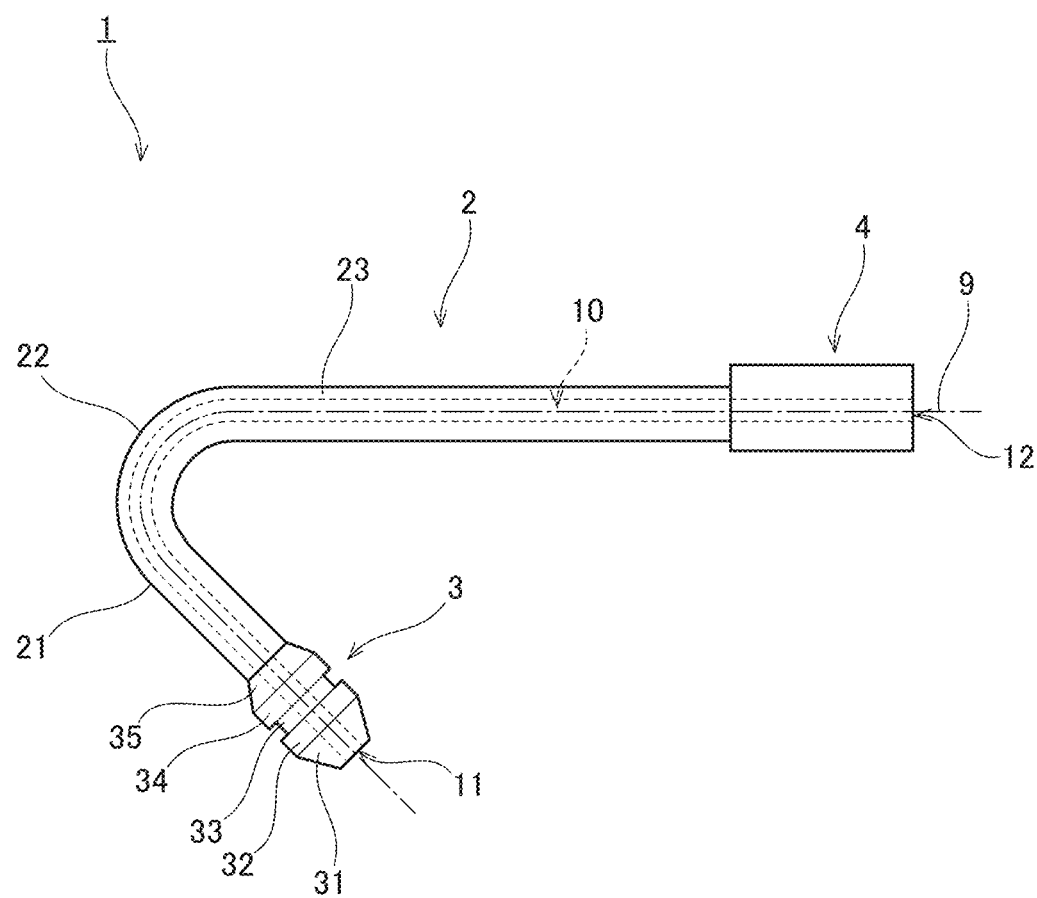
FIG. 2 is a side view of the catheter connecting member according to the first embodiment.
Figure 3:
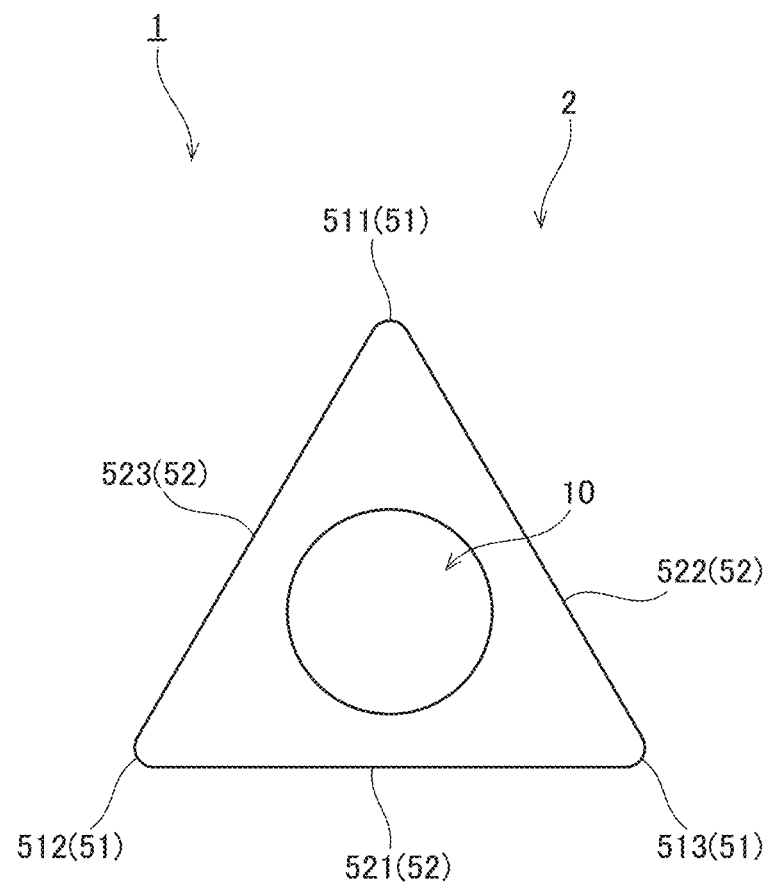
FIG. 3 is a cross-sectional view of a body unit of the catheter connecting member according to the first embodiment.

FIG. 1 is a perspective view of a catheter connecting member 1 according to a first embodiment of the present invention. FIG. 2 is a side view of the catheter connecting member 1. FIG. 3 is a cross-sectional view of a body unit 2 of the catheter connecting member 1. The catheter connecting member 1 of this embodiment is a member to be attached to the tip of a catheter and to be inserted into a vessel of a donor organ. The catheter connecting member 1 functions as an anastomosis assist tool for increasing workability of surgery in the field of vascular anastomosis.

As shown in FIGS. 1 and 2, the catheter connecting member 1 includes the body unit 2, an insertion unit 3, and a base end unit 4.

The body unit 2 is a tubular unit extending in a predetermined advancing direction. An axis indicating the advancing direction of the body unit 2 is called an advancing axis 9. The insertion unit 3 and the base end unit 4 are further arranged along the advancing axis 9. The body unit 2 has an approximately constant cross-sectional shape in a plane perpendicular to the advancing axis 9. As shown in FIG. 3, the cross section of the body unit 2 of this embodiment has an approximately regular triangular shape.

The cross section of the body unit 2 includes three projections 51 corresponding to the corners of a triangle, and three sides 52 of linear shapes connecting the projections 51. In a cross section perpendicular to the advancing axis 9, the projections 51 project outwardly. The projections 51 extend in the advancing direction of the body unit 2. Namely, the projections 51 extend along the advancing axis 9. More specifically, the three projections 51 include a first corner 511, a second corner 512, and a third corner 513. The three sides 52 include a first side 521 facing the first corner 511, a second side 522 facing the second corner 512, and a third side 523 facing the third corner 513. In this way, the body unit 2 in its entirety includes the projections 51. Further, the body unit 2 forms an anastomosis assist part having an approximately constant cross-sectional shape in a plane perpendicular to the advancing direction.

As shown in FIG. 2, the advancing axis 9 of the body unit 2 includes a linearly extending part, a part bent into a curved shape, and a linearly extending part arranged in this order as viewed from the tip toward the rear end. Thus, the body unit 2 includes a first linear part 21 extending in a linear shape, a bent part 22 bent into a curved shape, and a second linear part 23 extending in a linear shape arranged in this order as viewed from the tip toward the rear end.

In this embodiment, the first corner 511 is arranged at the innermost position at the bent part 22. Consequently, the first side 521 is arranged at the outermost position at the bent part 22. In this embodiment, the angle of the advancing direction of the body unit 2 changes by about 120° at the bent part 22.

The insertion unit 3 is arranged at the tip of the body unit 2. The insertion unit 3 includes a first tapered part 31, a first cylindrical part 32, a second cylindrical part 33, a third cylindrical part 34, and a second tapered part 35 arranged in this order as viewed from the tip toward the base end. The insertion unit 3 is inserted into one of two vessels to be anastomosed for implementation of anastomosis surgery.

The first tapered part 31 has an outer peripheral surface formed into a circular conical surface with an outer diameter increasing gradually from the tip. As a result, when the insertion unit 3 is inserted into a vessel from the tip, the insertion without placing load on the vessel is facilitated.

The first cylindrical part 32, the second cylindrical part 33, and the third cylindrical part 34 are arranged closer to the rear end than the first tapered part 31. Each of the first cylindrical part 32 and the third cylindrical part 34 has a cylindrical outer peripheral surface of an outer diameter same as the maximum outer diameter of the first tapered part 31. This allows the inner wall of a vessel to tightly contact the outer peripheral surfaces of the first cylindrical part 32 and the third cylindrical part 34 when the insertion unit 3 is inserted into the vessel.

The second cylindrical part 33 has a cylindrical outer peripheral surface of a smaller outer diameter than the first cylindrical part 32 and the third cylindrical part 34. Thus, when a vessel is ligated at the second cylindrical part 33, the ligated site becomes unlikely to deviate in the direction of the advancing axis 9. A position for ligation is not limited to the second cylindrical part 33. For example, a vessel may be ligated at a position slightly closer to the rear end than the second tapered part 35 and around a tip side end portion of the body unit 2.

In this embodiment, the second cylindrical part 33 of a small outer diameter is arranged between the first cylindrical part 32 and the third cylindrical part 34 having the same outer diameter. Alternatively, these parts may be configured as a single cylindrical part having an approximately constant outer diameter. By the provision of the cylindrical part having a cylindrical outer peripheral surface to the insertion unit 3, it becomes possible to ligate a vessel easily at this part of the insertion unit 3.

The second tapered part 35 has an outer peripheral surface of a diameter decreasing gradually from the rear end of the third cylindrical part 34 toward the body unit 2. By the presence of the tapered part at the rear end of the insertion unit 3, when the insertion unit 3 is pulled out of a vessel, the pulling-out without placing load on the vessel is facilitated.

The base end unit 4 is arranged at the rear end of the body unit 2. The base end unit 4 has a cylindrical outer peripheral surface. For connecting the catheter connecting member 1 to a catheter, the base end unit 4 functions as a connection to the catheter. A destination of connection of the catheter connecting member 1 is not limited to a catheter. The catheter connecting member 1 may also be connected to a fitting, a connector, or a tube other than a catheter, for example.

The catheter connecting member 1 includes a lumen 10 extending from the tip toward the rear end along the advancing axis 9. The tip of the catheter connecting member 1, namely, the tip of the insertion unit 3 is provided with a first opening 11. The rear end of the catheter connecting member 1, namely, the rear end of the base end unit 4 is provided with a second opening 12. The lumen 10 passes through the interior of the catheter connecting member 1 between the first opening 11 and the second opening 12. Namely, the lumen 10 connects the first opening 11 and the second opening 12.

Thus, when the base end unit 4 is connected to a catheter, a lumen in the catheter communicates with the first opening 11 through the second opening 12 and the lumen 10. This allows supply of a liquid such as a perfusate into a vessel or sucking of the liquid from the interior of the vessel.

The catheter connecting member 1 itself may be used as a catheter. More specifically, the rear end of the catheter connecting member 1 may directly be connected to a source of a liquid such as a perfusate or a liquid sucking mechanism. In this case, a liquid such as a perfusate can also be supplied into a vessel or the liquid can also be sucked from the interior of the vessel.

As shown in FIG. 3, the lumen 10 of this embodiment has a circular cross-sectional shape in a plane perpendicular to the advancing axis 9. The cross-sectional shape of the lumen 10 is approximately constant from the first opening 11 to the second opening 12. This suppresses increase in a resistance at a liquid flow path in the lumen 10.

The catheter connecting member 1 of this embodiment is integrally formed. Namely, the body unit 2, the insertion unit 3, and the base end unit 4 are formed as one member. The body unit 2, the insertion unit 3, and the base end unit 4 may be configured using different members.

In this embodiment, the body unit 2 has flexibility. The body unit 2 having flexibility is made of flexible resin, rubber, or elastomer, for example. More specifically, the flexible resin to be used is silicon resin such as silicon resin for medical purposes or epoxy resin, for example. This reduces the occurrence of damage on a vessel even when the catheter connecting member 1 is moved while the catheter connecting member 1 is inserted in the vessel. This also facilitates move of the catheter connecting member 1 to an intended position during surgery.

The body unit 2 may be configured not to be flexible. In this case, the body unit 2 may be made of polypropylene, polycarbonate, stainless steel, or titanium, for example.

During use of the catheter connecting member 1, the insertion unit 3 in its entirety and at least a part of the body unit 2 are inserted into a vessel. With the body unit 2 located at a position of anastomosis of vessels, the vessel in which the catheter connecting member 1 is inserted and the other vessel are anastomosed. The catheter connecting member 1 is mainly used for continuous suture in end-to-end anastomosis, end-to-side anastomosis, side-to-end anastomosis, or side-to-side anastomosis of vessels.

When the body unit 2 is inserted into a vessel, the vessel is widened with the projections 51 of the body unit 2 from the interior toward the exterior of the vessel. This can make it unlikely that the vessel will be flattened and the inner walls of the vessel will unintentionally stick to each other. If the body unit 2 is too thin for the vessel, it becomes difficult to widen the vessel in this way. By contrast, if the body unit 2 is too thick for the vessel, heavy load is applied to the vessel at points contacting the projections 51 and the body unit 2 and the vessel adhere each other even at a point not contacting the projection 51, causing the risk of failing to perform anastomosis successfully. In this regard, the diameter of the circumscribed circle of the body unit 2 in a cross section in a plane perpendicular to the advancing axis 9 is preferably in a range from 60 to 80% of the vascular size (diameter) of a vessel to receive insertion of the catheter connecting member 1 determined when the vessel is in a natural flowing state in a biological body. In this range, the vessel can be widened appropriately with the projections 51, while the probability of adherence between the body unit 2 and the catheter connecting member 1 can be reduced at a point not contacting the projection 51.

If at least a part of the catheter connecting member 1 has flexibility, this part preferably has hardness greater than the hardness of a vessel into which the catheter connecting member 1 is to be inserted. More specifically, the body unit 2 is preferably A 50 or more and less than D 80 according to the definition of JIS K 6253. When the body unit 2 is inserted into a vessel, the hardness of the body unit 2 falling within this range allows widening of the vessel from the interior toward the exterior of the vessel with the projections 51 and allows the catheter connecting member 1 to move easily during vascular anastomosis.

<1-2. Flow of Vascular Anastomosis Surgery>

Figure 4:
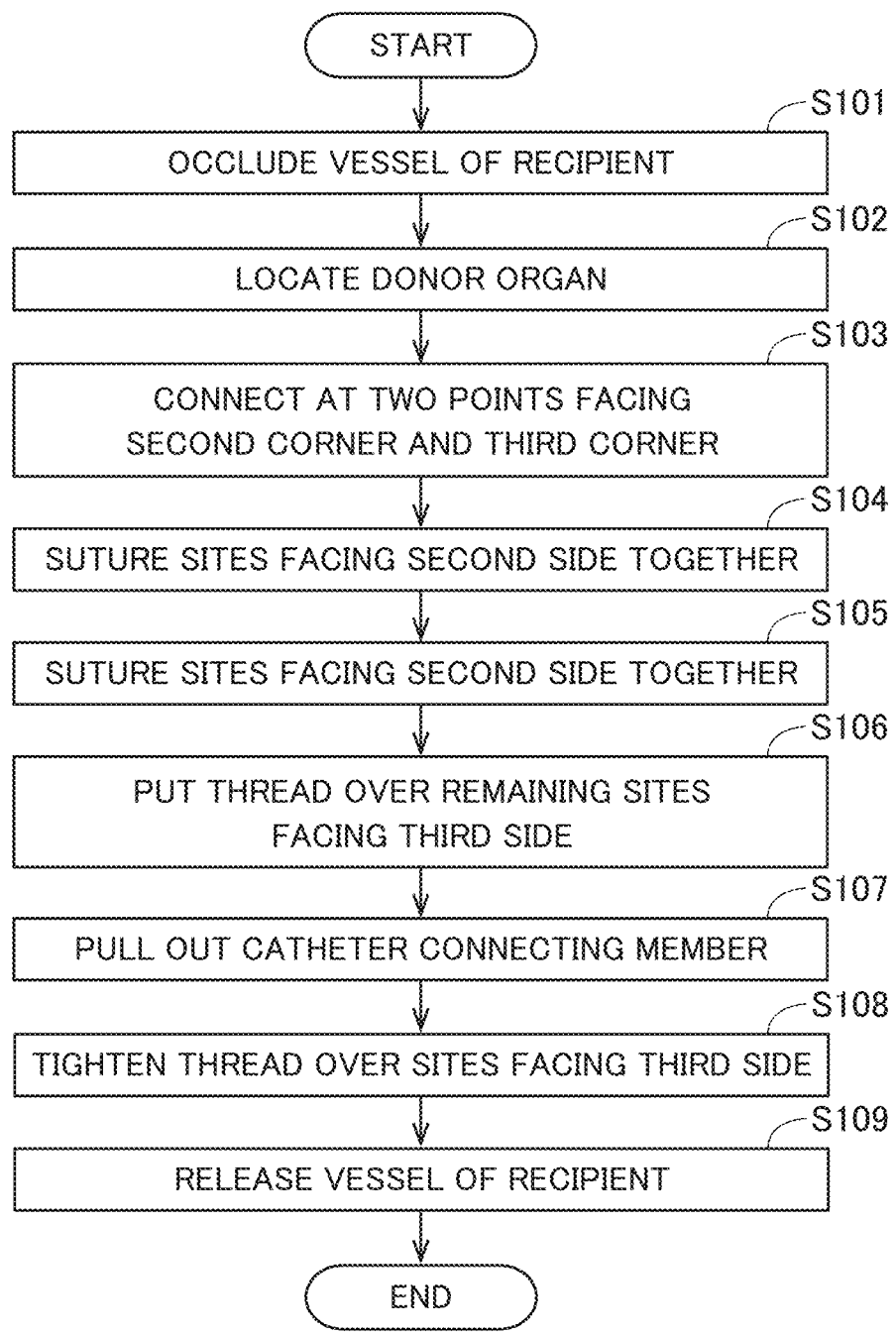
FIG. 4 is a flowchart showing a flow of exemplary vascular anastomosis surgery.

A flow of vascular anastomosis surgery using the catheter connecting member 1 will be described next by referring to FIGS. 4 to 8. FIG. 4 is a flowchart showing a flow of exemplary vascular anastomosis surgery using the catheter connecting member 1. FIGS. 5 to 8 show how the exemplary vascular anastomosis surgery is performed. In each of FIGS. 5 to 8, a photograph in the upper region shows how the vascular anastomosis surgery is performed, and a view in the lower region shows principal parts of the photograph.

The vascular anastomosis surgery shown in FIG. 4 is surgery for anastomosis of a first vessel 81 of a donor organ to a second vessel 82 of a recipient.

As shown in FIG. 4, the second vessel 82 of the recipient is occluded in advance with a clamp, for example (step S101). Meanwhile, a perfusate is supplied to the donor organ through the catheter connecting member 1 inserted in the first vessel 81 and a catheter connected to the catheter connecting member 1. While the catheter connecting member 1 is inserted in the first vessel 81 and the perfusate flows, the donor organ is located at a position for transplant (step S102). At this time, the insertion unit 3, the first linear part 21 of the body unit 2, and a part of the bent part 22 of the body unit 2 of the catheter connecting member 1 are inserted in the first vessel 81. The first vessel 81 is ligated to the insertion unit 3 of the catheter connecting member 1.

In this state, the first vessel 81 has an approximately regular triangular cross-sectional shape conforming to the outer peripheral surface of the body unit 2 of the catheter connecting member 1. At this time, the inner wall of the first vessel 81 receives strong force of widening the first vessel 81 outwardly applied at a point P1 contacting the first corner 511, a point P2 contacting the second corner 512, and a point P3 contacting the third corner 513. This avoids application of large tension to a site facing the first side 521, a site facing the second side 522, and a site facing the third side 523 of the inner wall of the first vessel 81, while controlling force of sticking to the outer peripheral surface of the body unit 2 at relatively low. Thus, when the catheter connecting member 1 is inserted in the first vessel 81, a surgical needle is hooked easily to a part of the first vessel 81 between the projections 51.

Figure 5:
FIG. 5 shows how the exemplary vascular anastomosis surgery is performed.
Figure 5:
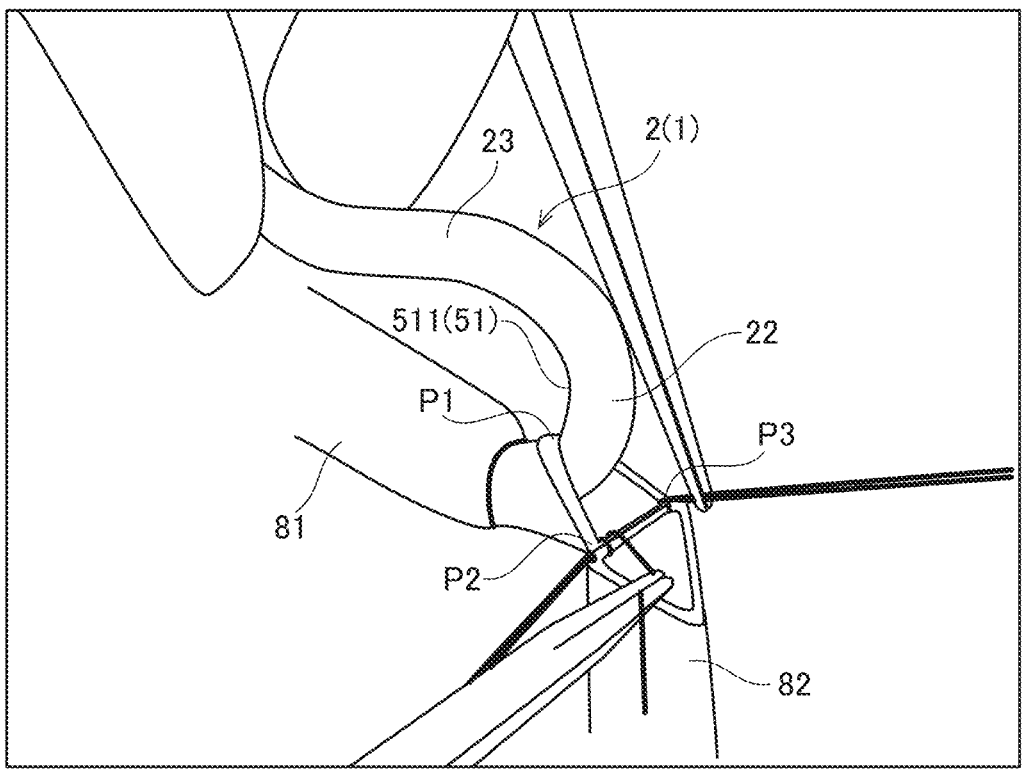

As shown in FIG. 5, in this embodiment, while an end portion as an anastomosis point of the first vessel 81 and an end portion as an anastomosis point of the second vessel 82 are located at predetermined positions, the first corner 511 of the first linear part 21 is located at a higher position. By doing so, the body unit 2 extending externally from the first vessel 81 is bent upwardly at the bent part 22. Further, the second linear part 23 is located above the first vessel 81.

As described above, the presence of the bent part 22 of the body unit 2 prevents a part of the catheter connecting member 1 located outside the first vessel 81 from extending above a site from the point P2 to the point P3 where the first vessel 81 and the second vessel 82 are to be anastomosed. This reduces the probability of hindrance to the vascular anastomosis surgery. As a result, working efficiency of the vascular anastomosis surgery is increased.

As described above, in the catheter connecting member 1 of this embodiment, the angle of the advancing direction of the body unit 2 changes by 120° at the bent part 22. In this way, the angle of the advancing direction of the body unit 2 preferably changes in a range from 90 to 180° at the bent part 22. This reduces the probability that the second linear part 23 or the base end unit 4 will overlap a position of anastomosis of the first vessel 81 and the second vessel 82. Even in the absence of the bent part 22, the body unit 2 can still be bent upwardly if the body unit 2 has flexibility.

After the anastomosis point of the first vessel 81 and the anastomosis point of the second vessel 82 are located at the predetermined positions, the first vessel 81 and the second vessel 82 are connected at two points with threads (step S103). More specifically, a surgical needle is hooked to the point P2 of the first vessel 81 facing the second corner 512 and a corresponding point of the second vessel 82, and these points are connected with a suture thread. Likewise, a surgical needle is hooked to the point P3 of the first vessel 81 facing the third corner 513 and a corresponding point of the second vessel 82, and these points are connected with a suture thread.

Next, sites between the point P2 and the point P3 are sutured together (step S104). More specifically, a site of the first vessel 81 facing the first side 521 of the body unit 2 and a corresponding site of the second vessel 82 are sutured together. At this time, as shown in FIG. 5, while the body unit 2 is pulled toward the direction of the first corner 511 (namely, upward direction), the sites between the point P2 and the point P3 are sutured continuously.

In step S104, the body unit 2 is arranged so as to place the first corner 511 on a near side in an operative field. By doing so, the site of the first vessel 81 from the point P2 facing the second corner 512 to the point P3 facing the third corner 513 is defined as a rear wall. Pulling the body unit 2 toward the direction of the first corner 511 expands a viewing field around the rear walls of the first vessel 81 and the second vessel 82 (between the point P2 and the point P3). This allows the rear walls of the first vessel 81 and the second vessel 82 to be sutured together from inside (from the intima).

During vascular anastomosis for organ transplant, vessels are generally anastomosed from outside the vessels (from the adventitia). If a margin of suture for anastomosis is short like in the case of vascular anastomosis of suprahepatic inferior vena cava for liver transplant, for example, it is difficult to reverse vessels for suture of their rear wall sides. This necessitates suture of the rear walls of the vessels from inside. Compared to suture of the vessels from outside, suture of the vessels from inside should proceed with great care so as not to damage the intimae of the vessels. During suture of the rear walls, care should also be taken so as to prevent a surgical needle from being hooked to the front walls of the vessels. For these reasons, it becomes necessary to ensure a sufficient viewing field around a suture site. In this case, pulling the front wall of the vessel with tweezers, for example, for ensuring a viewing field causes the risk of damage on the vessel near the front wall.

In this regard, as shown in FIG. 5, in the use of the catheter connecting member 1, pulling the front wall of the first vessel 81 upwardly by pulling the body unit 2 toward the direction of the first corner 511 makes it possible to expand a viewing field around the rear walls of the first vessel 81 and the second vessel 82. In this case, the body unit 2 contacts a wide range inside the vessel during the upward pulling, allowing significant reduction in damage on the vessel compared to pulling of the vessel with tweezers, for example. As described above, in step S104, suture preferably proceeds while the body unit 2 is pulled toward the direction of the first corner 511.

Figure 6:
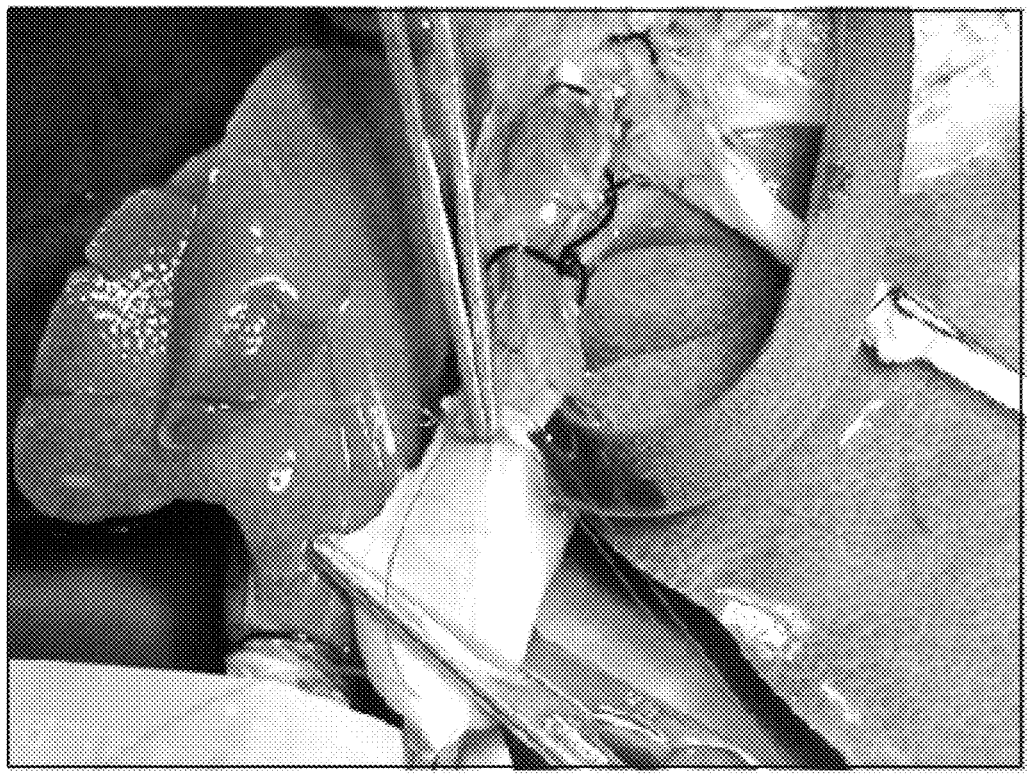
FIG. 6 shows how the exemplary vascular anastomosis surgery is performed.
Figure 6:
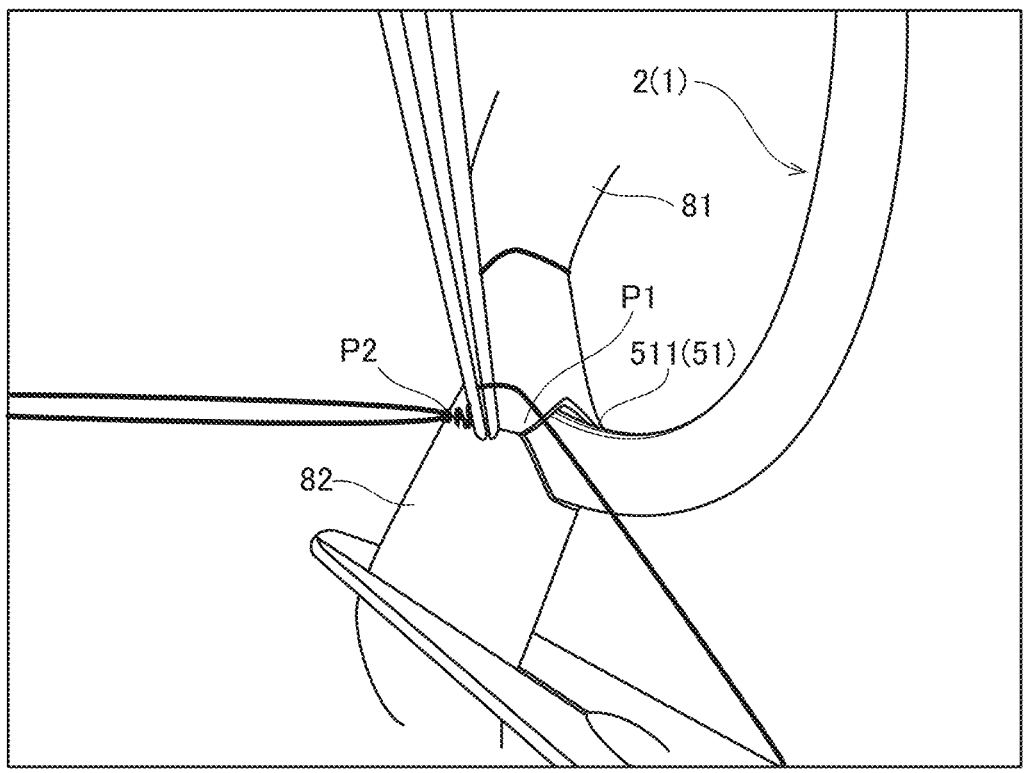

Next, as shown in FIG. 6, sites between the point P1 and the point P2 are sutured together (step S105). More specifically, a site of the first vessel 81 facing the third side 523 of the body unit 2 and a corresponding site of the second vessel 82 are sutured together. At this time, while the body unit 2 is pulled toward the direction of the third corner 513, the sites between the point P1 and the point P2 are sutured continuously. This facilitates suture of sites around the third side 523.

In step S105, the sites from the point P2 to the point P1 (left walls of the first vessel 81 and the second vessel 82) are continuously sutured together from outside. In doing so, the first vessel 81 is widened outwardly at the point P1 contacting the first corner 511 and the point P2 contacting the second corner 512. This makes it unlikely that the first vessel 81 will stick to the body unit 2 between the point P1 and the point P2. In this state, a surgical needle is hooked easily to the sites from the point P2 to the point P1 from outside the first vessel 81 and the second vessel 82.

Then, a surgical needle is hooked to remaining sites between the point P1 and the point P3 and a suture thread is put over these sites (step S106). More specifically, the suture thread is put between a site of the first vessel 81 facing the second side 522 of the body unit 2 and a corresponding site of the second vessel 82.

In step S106, the sites from the point P1 to the point P3 (right walls of the first vessel 81 and the second vessel 82) are continuously sutured together partially from outside in a direction from the point P1 toward the point P3. At this time, the suture thread is not tightened but is kept in a loosened state. At this time, the body unit 2 may be pulled toward the direction of the second corner 512 during the suture. In this case, the right wall of the first vessel 81 is separated from the body unit 2. By doing so, the surgical needle is hooked more easily to the first vessel 81 at the site between the point P1 and the point P3.

Figure 7:
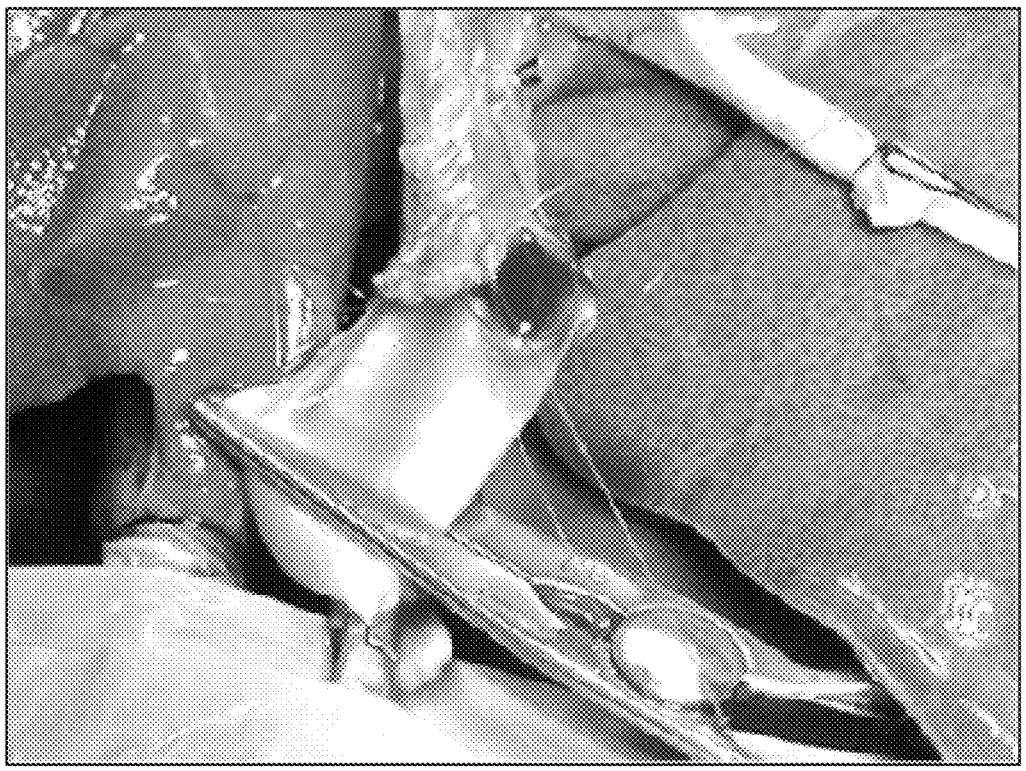
FIG. 7 shows how the exemplary vascular anastomosis surgery is performed.
Figure 7:
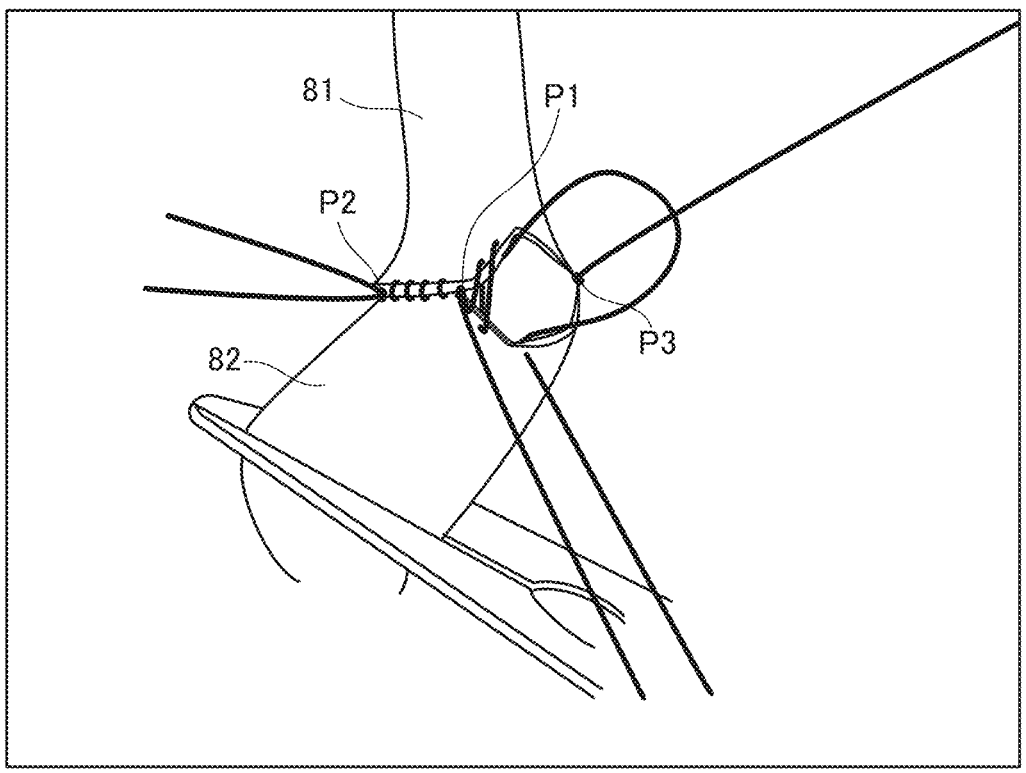
Figure 8:
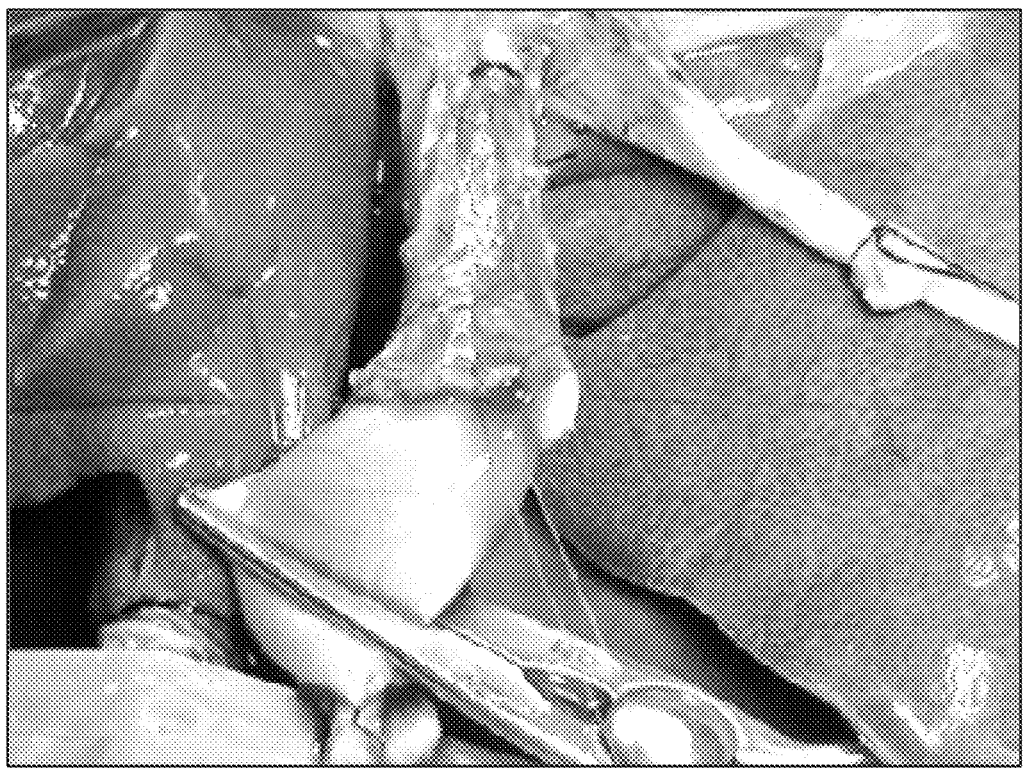
FIG. 8 shows how the exemplary vascular anastomosis surgery is performed.
Figure 8:
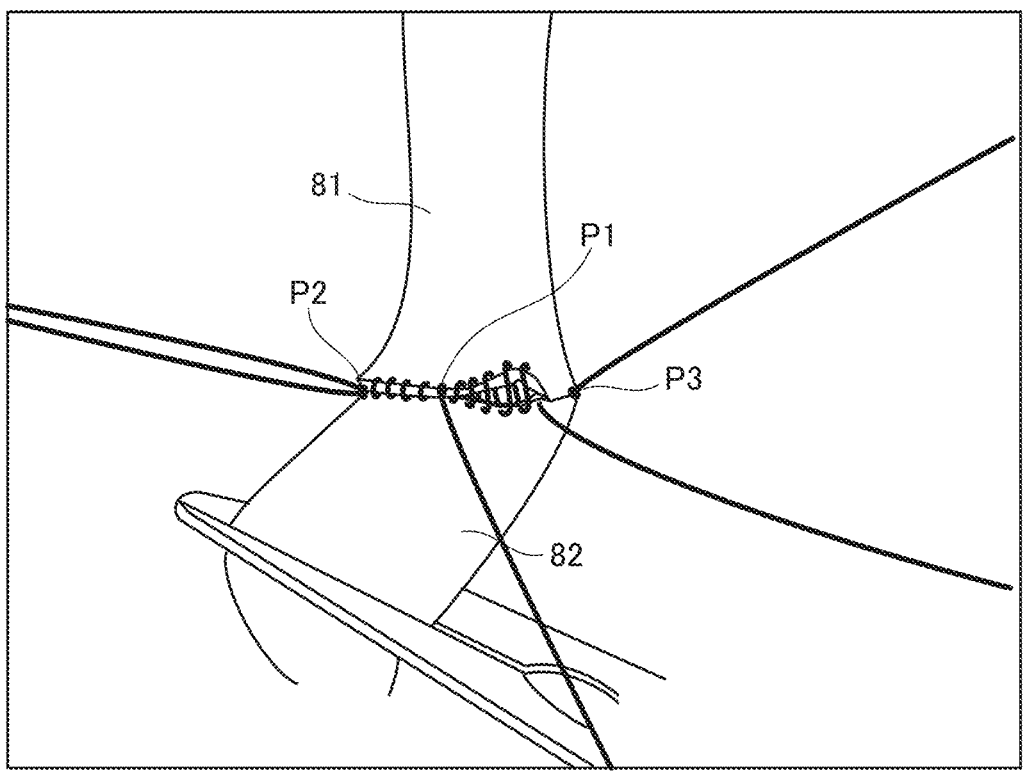

Next, while a perfusate is supplied through the first opening 11, the catheter connecting member 1 is pulled out of the first vessel 81 (step S107). FIG. 7 shows a state immediately after the catheter connecting member 1 is pulled out in step S107. Shortly thereafter, the suture thread put between the point P1 and the point P3 is tightened (step S108). FIG. 8 shows a state where the suture thread is being tightened in step S108. If there are sites between the point P1 and the point P3 left without being sutured, these sites are successively subjected to the continuous suture. By doing so, the sites between the point P1 and the point P3 are sutured together. In this way, the first vessel 81 and the second vessel 82 are sutured together along their entire peripheries to finish anastomosis of the first vessel 81 and the second vessel 82.

Finally, the clamp and others are removed to restore a flow of blood in the second vessel 82 of the recipient (step S109). By doing so, a blood flow is generated between the first vessel 81 and the second vessel 82.

As described above, for suture of the site of the first vessel 81 facing the first side 521 in step S104, the body unit 2 is pulled toward the direction of the first corner 511 to separate the rear wall to be sutured from the catheter connecting member 1 and the front wall. Likewise, for suture of the site of the first vessel 81 facing the third side 523 in step S105, the body unit 2 is pulled toward the direction of the third corner 513 to separate the left wall to be sutured from the catheter connecting member 1. Further, for putting of the suture thread over the site of the second vessel 81 facing the second side 522 in step S106, the body unit 2 is pulled toward the direction of the second corner 512 to separate the right wall to be sutured from the catheter connecting member 1. In this way, suture of the first vessel 81 and the second vessel is facilitated. Namely, compared to the conventional triangular anastomosis surgery, workability of surgery is increased.

According to this embodiment, like in the conventional triangular anastomosis surgery, each of the first vessel 81 and the second vessel 82 are divided into three suture regions for suture. In this case, as each suture region of the first vessel 81 is located between the projections 51, a surgical needle is hooked easily to a corresponding site. Thus, even when a catheter for supply or suction of a perfusate is connected to the first vessel 81 to be anastomosed, workability of surgery is still unlikely to be reduced.

The three suture regions formed between the three projections 51 each have a length of about one-third of the entire periphery of a vessel. This achieves continuous suture over a region of a comparatively great length of about one-third of the entire periphery of the vessel. If there are a large number of finely divided regions each defined as a region allowing continuous suture, the number of points to be ligated with a suture thread is increased to cause a problem of an extended duration of vascular anastomosis. In this regard, the number of the projections 51 is preferably two, three, or four. This achieves continuous suture over a region of a comparatively great length of about one-fourth or more of the entire periphery of a vessel in each suture region. As a result, it becomes possible to shorten a duration of vascular anastomosis. According to vascular anastomosis surgery by means of the conventional triangular anastomosis, a duration of the vascular anastomosis is about 15 minutes. By contrast, according to vascular anastomosis surgery using the catheter connecting member 1 as an anastomosis assist tool, a duration of the vascular anastomosis can be shortened to about five minutes.

The foregoing vascular anastomosis surgery performed while a perfusate is supplied to the first vessel 81 allows shortening of a duration of ischemia in a donor organ. According to the vascular anastomosis surgery by means of the conventional triangular anastomosis performed in the absence of a connected catheter, a duration of ischemia in a donor organ is about 15 minutes, which is equal to a duration of the vascular anastomosis. By contrast, the vascular anastomosis surgery using the catheter connecting member 1 as an anastomosis assist tool allows supply of a perfusate during implementation of the vascular anastomosis surgery, making it possible to shorten a duration of ischemia in a donor organ further to a duration less than a duration of the vascular anastomosis, which is about five minutes.

According to the conventional vascular anastomosis surgery, to reduce the occurrence of mixing of air bubbles into a vessel, a liquid such as physiological saline solution is required to be supplied into the vessel using a syringe, for example, immediately before suture of a last site. By contrast, according to this embodiment, immediately after the catheter connecting member 1 is pulled out in step S107 while a perfusate is supplied to the first vessel 81, the last sites can be sutured together in step S108. This allows omission of a step of supplying a liquid into a vessel using a syringe, for example. As a result, workability of surgery is increased.

According to this embodiment, the body unit 2 is a regular triangle in a cross section. The "regular triangle" mentioned in the present invention includes an "approximately regular triangle." To be more specific, the catheter connecting member 1 of this embodiment is an approximately regular triangle with the rounded first corner 511, the rounded second corner 512, and the rounded third corner 513 corresponding to the three projections 51. These three projections 51 are arranged uniformly in a peripheral direction. The "peripheral direction" mentioned herein means a direction along the circumference of a circle centered on the advancing axis 9. If the catheter connecting member 1 is inserted into a vessel in a wrong direction, uniformly arranging the projections 51 facilitates adjustment of the direction of the insertion.

According to this embodiment, the body unit 2 in its entirety forms an anastomosis assist part including the projections 51 and having an approximately constant cross-sectional shape in a plane perpendicular to the advancing axis 9. However, this is not intended to limit the present invention. The anastomosis assist part with a projection may be configured using only a part of the body unit 2. For example, only the first linear part 21 of the body unit 2 may function as an anastomosis assist part with the projections 51, and the other part of the body unit 2 may have a cylindrical outer peripheral surface. Alternatively, only the first linear part 21 and the bent part 22 of the body unit 2 may function as an anastomosis assist part with the projections 51.

2. Modifications

While the one embodiment of the present invention has been described hereinabove, the present invention is not limited to the foregoing embodiment.

Figure 9:
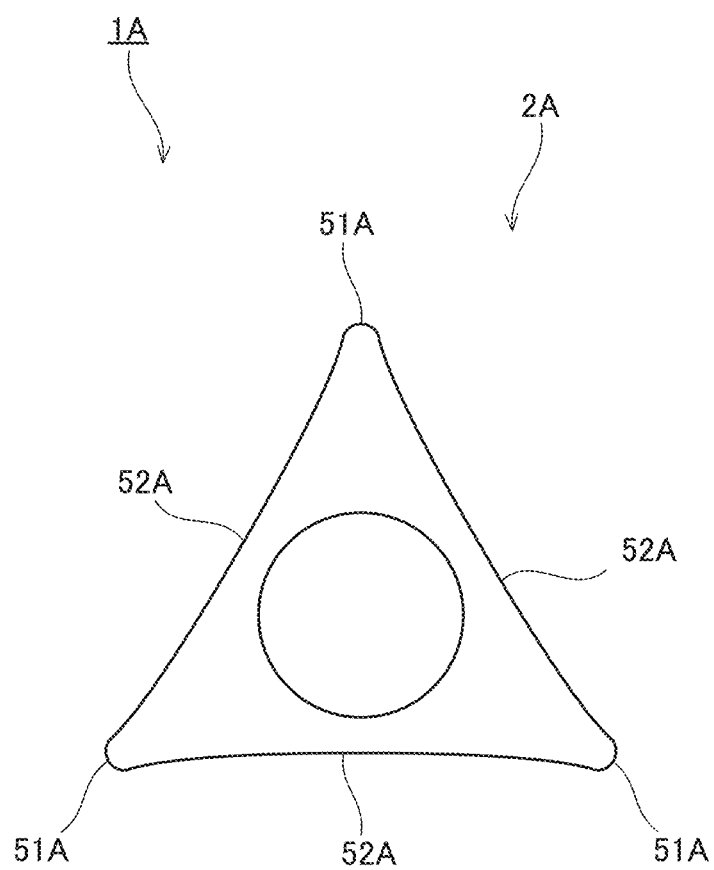
FIG. 9 is a cross-sectional view of a body unit of a catheter connecting member according to a modification.

FIG. 9 is a cross-sectional view of a body unit 2A of a catheter connecting member 1A according to a modification. The body unit 2A of the catheter connecting member 1A in the illustration of FIG. 9 includes three projections 51 arranged at uniform intervals in a peripheral direction. In the catheter connecting member 1A, a side 52A between two of projections 51A adjacent to each other in the peripheral direction extends not in a linear shape but in a curved shape recessed inwardly. Thus, when a vessel is located along the outer periphery of the body unit 2A, the probability of sticking of the vessel to the side 52A is reduced further, compared to the case of a linear side. This increases workability further during implementation of vascular anastomosis surgery.

Figure 10:
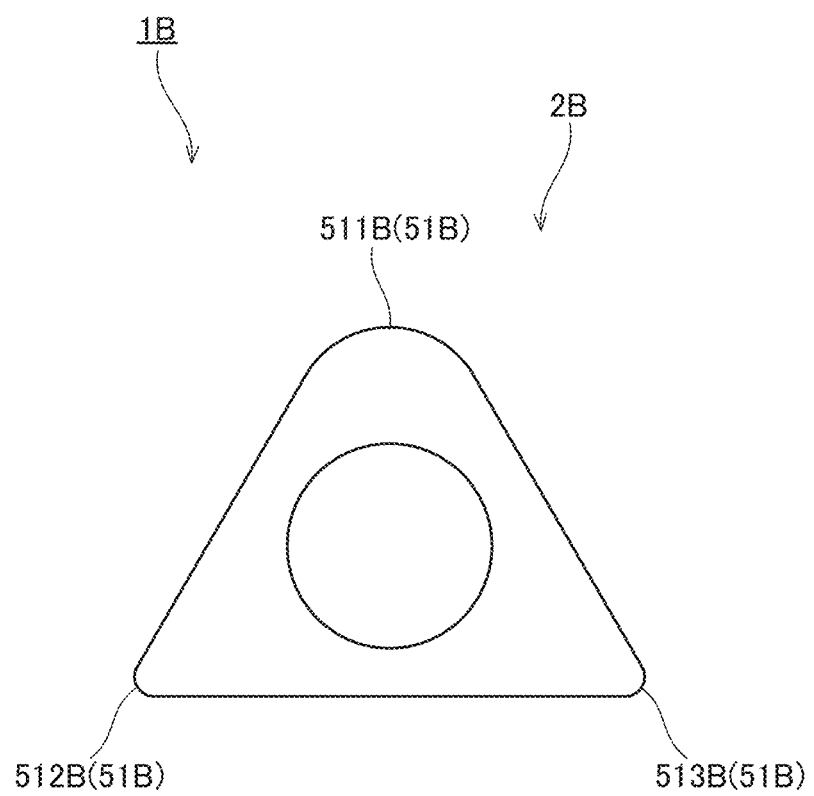
FIG. 10 is a cross-sectional view of a body unit of a catheter connecting member according to a modification.

FIG. 10 is a cross-sectional view of a body unit 2B of a catheter connecting member 1B according to a different modification. In the catheter connecting member 1B in the illustration of FIG. 10, a first corner 511B corresponding to one of three projections 51B has a different shape from a second corner 512B and a third corner 513B corresponding to the other two projections 51B. Like in this case, the projections are not always required to have the same shape.

Figure 11:
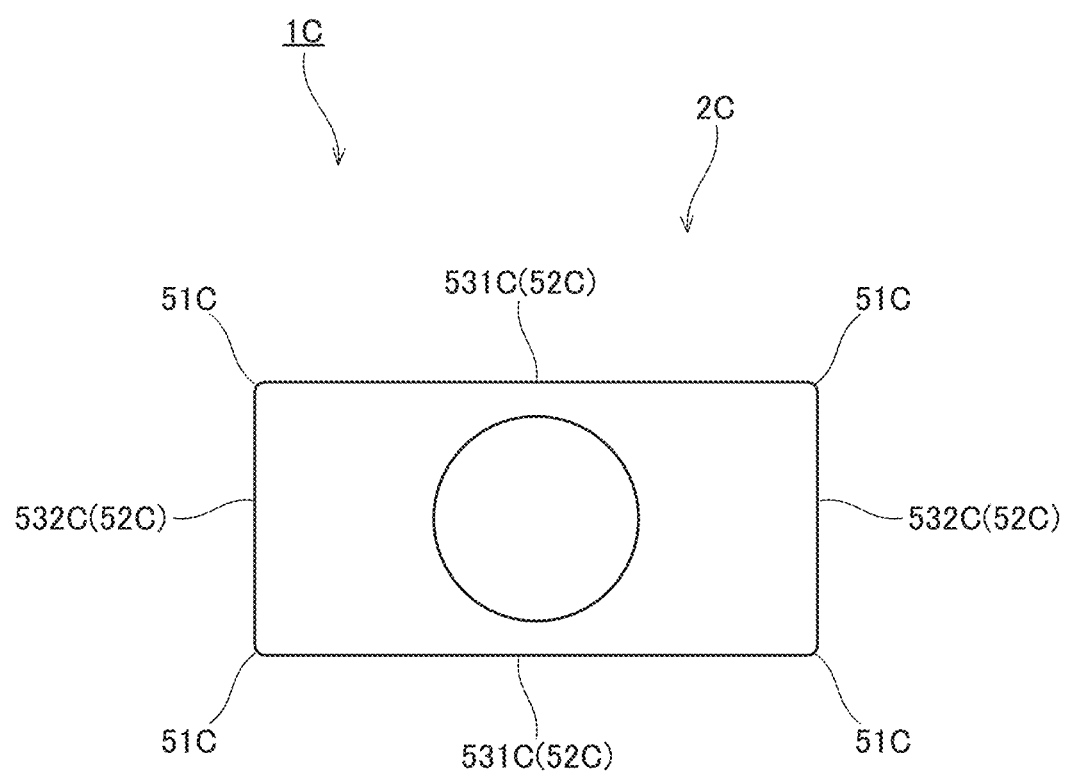
FIG. 11 is a cross-sectional view of a body unit of a catheter connecting member according to a modification.

FIG. 11 is a cross-sectional view of a body unit 2C of a catheter connecting member 1C according to a different modification. In the catheter connecting member 1C in the illustration of FIG. 11, the body unit 2C has a rectangular cross-sectional shape. The body unit 2C includes four projections 51C and four linear sides 52C. The four sides 52C include two long sides 531C and two short sides 532C.

When this catheter connecting member 1C is inserted into a vessel, the inner wall of the vessel receives strong force of widening the vessel outwardly applied to a point contacting each of the projections 51C. This avoids application of large tension to a site of the vessel facing the side 52C and controls force of sticking to the outer peripheral surface of the body unit 2C at relatively low. Force of sticking to the outer peripheral surface of the body unit 2 is particularly small at a site of the vessel facing the long side 531C. This facilitates suture of parts facing the long side 531C during implementation of vascular anastomosis surgery using the catheter connecting member 1C. Namely, workability is increased during implementation of the vascular anastomosis surgery. Like in the illustration of FIG. 11, the number of the projections 51C provided to the body unit 2C may be four.

The cross-sectional shape of a body unit with four projections is not always required to be a rectangle. The cross-sectional shape of the body unit may be a square or a rhombus, for example. Even in such cases, the inner wall of a vessel is still unlikely to stick to a side between the projections. This facilitates suture of parts facing the side to increase workability of vascular anastomosis surgery.

Figure 12:
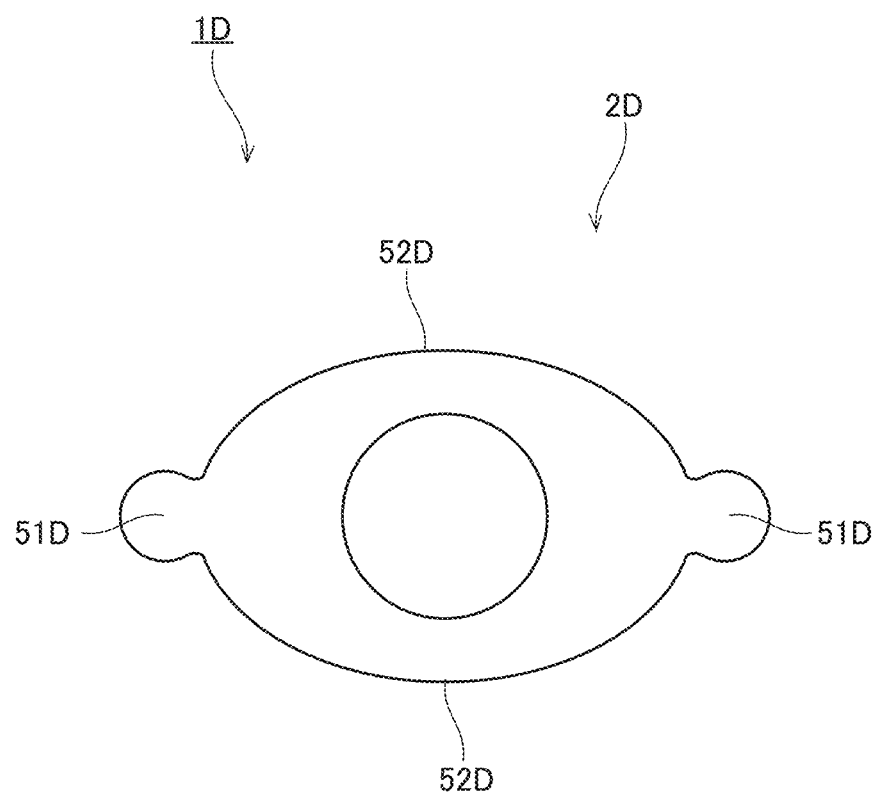
FIG. 12 is a cross-sectional view of a body unit of a catheter connecting member according to a modification.

FIG. 12 is a cross-sectional view of a body unit 2D of a catheter connecting member 1D according to a different modification. In the catheter connecting member 1D in the illustration of FIG. 12, the body unit 2D has an oval cross-sectional shape. The body unit 2D includes two projections 51D projecting in the direction of the major axis of the oval shape, and two curved sides 52D.

When this catheter connecting member 1D is inserted into a vessel, the inner wall of the vessel receives strong force of widening the vessel outwardly applied to a point contacting each of the projections 51D. This avoids application of large tension to a site of the vessel facing the side 52D and controls force of sticking to the outer peripheral surface of the body unit 2D at relatively low. This facilitates suture of parts facing the side 52D during implementation of vascular anastomosis surgery using the catheter connecting member 1D. Namely, workability is increased during implementation of the vascular anastomosis surgery. Like in the illustration of FIG. 12, the number of the projections 51D provided to the body unit 2D may be two.

In the foregoing embodiment, the shape of the body unit of the catheter connecting member is such that the bent part is arranged between the two linear parts. However, this is not the only shape of the body unit of the anastomosis assist tool according to the present invention. For example, the body unit may be formed only of a linear part, or may be formed of one linear part and one bent part. Alternatively, the body unit may be formed only of a curved part gently bent in its entirety. If appropriate, the shape of the body unit may be changed in response to location of a vessel during surgery into which the body unit is to be inserted, for example.

In the foregoing embodiment, the catheter connecting member is made only of elastomer. In the anastomosis assist tool of the present invention, however, a surface of the body unit 2 functioning as the anastomosis assist part may be subjected to surface treatment. Examples of the available surface treatment to be performed include surface lubricating treatment of reducing surface friction such as film coating, silicon-based thin film coating, Teflon (registered trademark) thin film coating, and surface chemical treatment for lower friction, and surface hardening treatment of increasing surface hardness. Implementation of the surface lubricating treatment makes it possible to reduce a coefficient of friction between the surface of the body unit 2 and a surgical needle. As a result, the occurrence of hooking of the surgical needle to the surface of the body unit 2 is reduced. Implementation of the surface hardening treatment makes it possible to reduce the occurrence of sticking of a surgical needle into the surface of the body unit 2. As a result, workability of vascular anastomosis surgery is increased.

The anastomosis assist tool used in the foregoing embodiment and modifications is the catheter connecting member having a lumen to be connected to a lumen in a catheter. Meanwhile, an anastomosis assist tool without a lumen is applicable to vascular anastomosis surgery. Even in this case, workability can still be increased and a duration of surgery can still be shortened, compared to triangular anastomosis surgery generally performed. As a result, it becomes possible to shorten a duration of an ischemia state during organ transplant.

The components described in the foregoing embodiment and modifications may be consistently combined together, as appropriate.

REFERENCE SIGNS LIST 1, 1A, 1B, 1C, 1D Catheter connecting member
2, 2A, 2B, 2C, 2D Body unit
3 Insertion unit
9 Advancing axis
10 Lumen
11 First opening
12 Second opening
21 First linear part
22 Bent part
23 Second linear part
31 First tapered part
32 First cylindrical part
33 Second cylindrical part
34 Third cylindrical part
35 Second tapered part
51, 51A, 51B, 51C, 51D Projection
52, 52A, 52C, 52D Side

The invention claimed is:

1. A vascular anastomosis method using an anastomosis assist tool, wherein said anastomosis assist tool comprising:
   a body unit extending in a predetermined advancing direction and having a part to be inserted into a vessel; and
   an insertion unit arranged at the tip of said body unit,
   said insertion unit includes a tapered part of a diameter decreasing gradually toward a tip,
   said body unit includes an anastomosis assist part having an approximately constant cross-sectional shape in a plane perpendicular to said advancing direction, the anastomosis assist part including three projections projecting outwardly as viewed in said cross section and extending in said advancing direction, and
   said three projections include a first corner, a second corner, and a third corner,
   the method comprising:
   a) a step of continuously suturing a site of a first vessel from a point facing said second corner to a point facing said third corner and a corresponding site of a second vessel together while said anastomosis assist tool is inserted in said first vessel; and
   b) a step of continuously suturing a site of said first vessel from a point facing said first corner to said point facing said second corner and a corresponding site of said second vessel together while said anastomosis assist tool is inserted in said first vessel.

2. The vascular anastomosis method according to claim 1, further comprising:
   c) a step of continuously suturing at least a part of a site of said first vessel from said point facing said first corner to said point facing said third corner and at least a part of a corresponding site of said second vessel together with a suture thread in a loosened state while said anastomosis assist tool is inserted in said first vessel, said step c) being performed after said step a) and said step b);
   d) a step of pulling said anastomosis assist tool out of said first vessel after said step c); and
   e) a step of tightening said suture thread after said step d).

3. The vascular anastomosis method according to claim 1, wherein
   in said step a), said first corner is placed on a near side in an operative field, and said site of said first vessel from said point facing said second corner to said point facing said third corner is defined as a rear wall.

4. The vascular anastomosis method according to claim 1, wherein
  the suture in said step a) proceeds while said body unit is pulled toward the direction of said first corner.

5. The vascular anastomosis method according to claim 1, wherein
  the suture in said step b) proceeds while said body unit is pulled toward the direction of said third corner.

6. The vascular anastomosis method according to claim 1, wherein
  said cross section of said anastomosis assist part is a regular triangle.

7. The vascular anastomosis method according to claim 1, wherein
  said projections are arranged uniformly in a peripheral direction.

* * * * *